(12) United States Patent
Baynham

(10) Patent No.: US 8,002,809 B2
(45) Date of Patent: Aug. 23, 2011

(54) DYNAMIC CERVICAL PLATE

(75) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 708 days.

(21) Appl. No.: 12/134,672

(22) Filed: Jun. 6, 2008

(65) Prior Publication Data

US 2008/0234681 A1  Sep. 25, 2008

Related U.S. Application Data

(63) Continuation-in-part of application No. 11/624,575, filed on Jan. 18, 2007, now Pat. No. 7,815,666, which is a continuation-in-part of application No. 10/776,369, filed on Feb. 10, 2004, now abandoned.

(51) Int. Cl.
*A61B 17/66* (2006.01)
*A61B 17/80* (2006.01)

(52) U.S. Cl. ........................................ 606/282; 606/289

(58) Field of Classification Search .................. 606/282, 606/289
See application file for complete search history.

(56) References Cited

U.S. PATENT DOCUMENTS

| | | | |
|---|---|---|---|
| 5,234,431 | A | 8/1993 | Keller |
| 5,545,164 | A | 8/1996 | Howland |
| 5,616,142 | A | 4/1997 | Yuan et al. |
| 5,620,443 | A | 4/1997 | Gertzbein et al. |
| 5,672,177 | A | 9/1997 | Seldin |
| 5,702,395 | A | 12/1997 | Hopf |
| 6,017,345 | A | 1/2000 | Richelsoph |
| 6,136,002 | A | 10/2000 | Shih et al. |
| 6,159,213 | A | 12/2000 | Rogozinski |
| 6,402,756 | B1 | 6/2002 | Ralph et al. |
| 6,689,134 | B2 | 2/2004 | Ralph et al. |
| 2002/0188296 | A1 | 12/2002 | Michelson |
| 2003/0060828 | A1 | 3/2003 | Michelson |
| 2003/0130661 | A1 | 7/2003 | Osman |
| 2004/0019353 | A1 | 1/2004 | Freid et al. |

*Primary Examiner* — Thomas C Barrett
*Assistant Examiner* — Sameh Boles
(74) *Attorney, Agent, or Firm* — McHale & Slavin, P.A.

(57) ABSTRACT

A dynamic cervical plate has a ratchet and pawl mechanism that allows the cervical plate to post operatively shorten the length of the plate and maintain compression between adjacent vertebrae. The plate has an elongated shaft with grooves on one surface and a groove along each longitudinal edge. A lateral bar is attached on one end of the shaft. The bar has screw holes for connecting with the head of a spinal screw. Another lateral bar is slidably engaged in the longitudinal grooves along the shaft and has a spring clip acting as a pawl with the grooves on the shaft. The sliding bar has screw holes on each side of the shaft. The clip is configured to span the screw holes to prevent screws from backing out of the holes.

17 Claims, 4 Drawing Sheets

DYNAMIC CERVICAL PLATE

RELATED APPLICATIONS

This application is a continuation-in-part of U.S. patent application Ser. No. 11/624,575 filed Jan. 18, 2007 now U.S. Pat. No. 7,815,666, which is a continuation-in-part of U.S. patent application Ser. No. 10/776,369 filed Feb. 10, 2004 now abandoned, the contents of which are incorporated herein by reference.

FIELD OF THE INVENTION

This invention relates to the field of orthopedic surgery and, particularly, to the area of spinal implants for stabilizing the spatial relationship of vertebrae. The device is designed for use in the cervical region of the spine though one skilled in the art may use the device in other regions of the spine and other skeletal fixations.

BACKGROUND OF THE INVENTION

Spinal plates are well known in the orthopedic art for fixing bones or bone fragments in a pre-selected spatial orientation. The plates are usually attached to the bones or bone fragments by screws designed to make a secure and long lasting connection not affected by the loads caused by normal activities of the host. Gertzbein et al, U.S. Pat. No. 5,620,443, teaches an adjustable cervical connector composed of dual rods spanning the distance between adjacent vertebrae. The rods carry at least two slidable transverse connectors which are attached to the vertebrae by spikes and bone screws thereby fixing the relationship of the bones. The connectors are immobilized on the rods by clamps.

Richelsoph, U.S. Pat. No. 6,017,345, teaches a spinal plate spanning the distance between adjacent vertebrae. The plate has screw holes in each end. The pedicle screws are inserted through the holes and allow for some movement.

Shih et al, U.S. Pat. No. 6,136,002, teaches a similar device to that of Gertzbein with the clamps screwed onto the elongated rods.

Published Patent Application US 2003/0060828 A1 to Michelson teaches a cervical plate with at least two plate elements slidably connected together and fixed by a set screw. The contacting surfaces of the plate elements are formed with ratcheting to provide added security.

In all these prior art devices, the plate must be held in the selected position while the securing set screws or other fasteners are put in place and the final assembly is completed.

What is needed in the art is a dynamic cervical plate that may be adjusted to length, locked in place to provide compression, and will automatically shorten its length to maintain compression.

SUMMARY OF THE PRESENT INVENTION

It is an objective of this invention to provide a cervical plate with an elongated shaft adapted to span the intervertebral space and having at least two bars spaced along the length of the plate. The bars each have countersunk screw holes for accepting the heads of bone screws resulting in a smooth surface.

Another objective of this invention is to provide a locking mechanism that is manually operated simultaneously with the insertion of bone screws in positioning of the bars along the plate to provide compression across the intervertebral space.

A further objective of this invention is to provide a locking mechanism with a retainer extending over the screw holes to prevent back-out of the screws.

Yet another objective of this invention is to provide a guide rail on the plate shaft cooperating with the bars to permit sliding connection between the bars and the plate shaft.

Still another objective of this invention is to provide a ratchet mechanism on the shaft to permit post operative one-way movement shortening the distance between the screw receivers and maintaining compression across the intervertebral space.

DETAILED DESCRIPTION OF THE INVENTION

Figure 1:
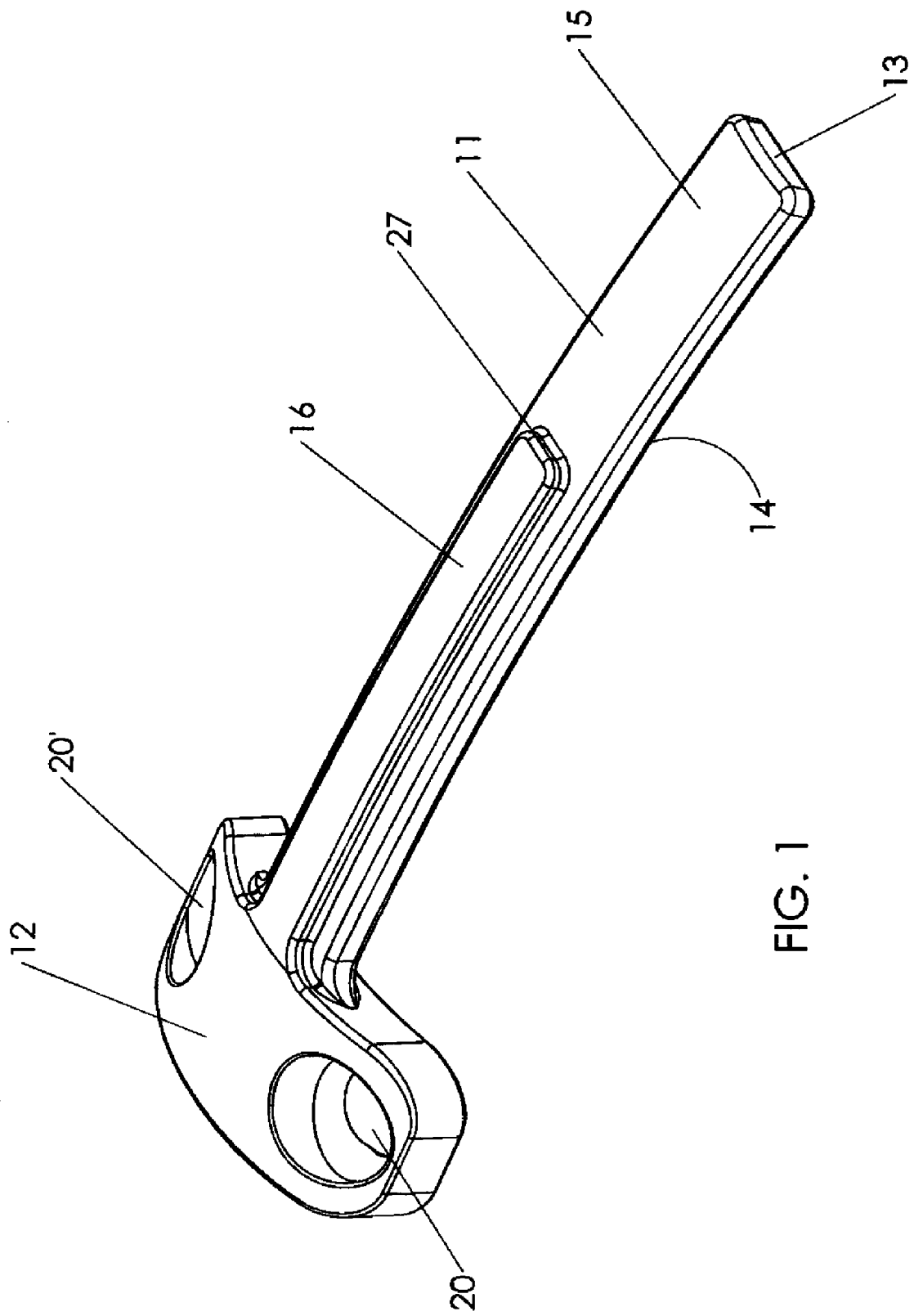
FIG. 1 is a perspective of the cervical plate.

The cervical plate 10, shown in FIG. 1, has an elongated shaft 11 that is made in different lengths but must be of a length to span, at least, the distance between two vertebrae. The shaft 11 has a lateral bar 12 fixed to one end and a free end 13. The shaft has a distal surface 14 for contacting the spine and a proximal surface 15. A longitudinal rail 16 extends from the lateral bar 12 and terminates short of the free end on the proximal surface. The lateral bar 12 has countersunk apertures 20, 20' on each side of the plate for capturing the heads of bone screws.

Figure 2:
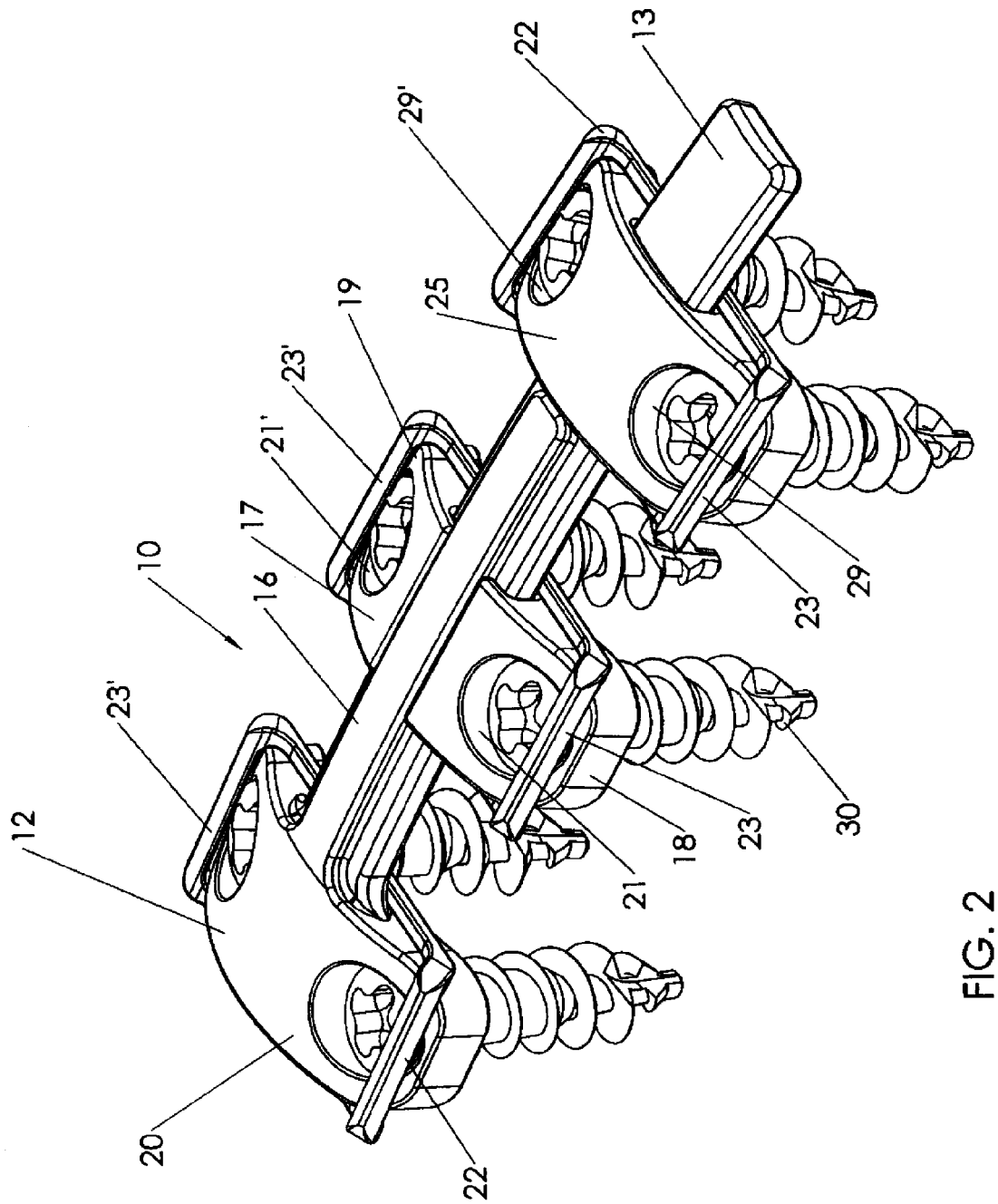
FIG. 2 is a top perspective view of the cervical plate and screw receivers.
Figure 3:
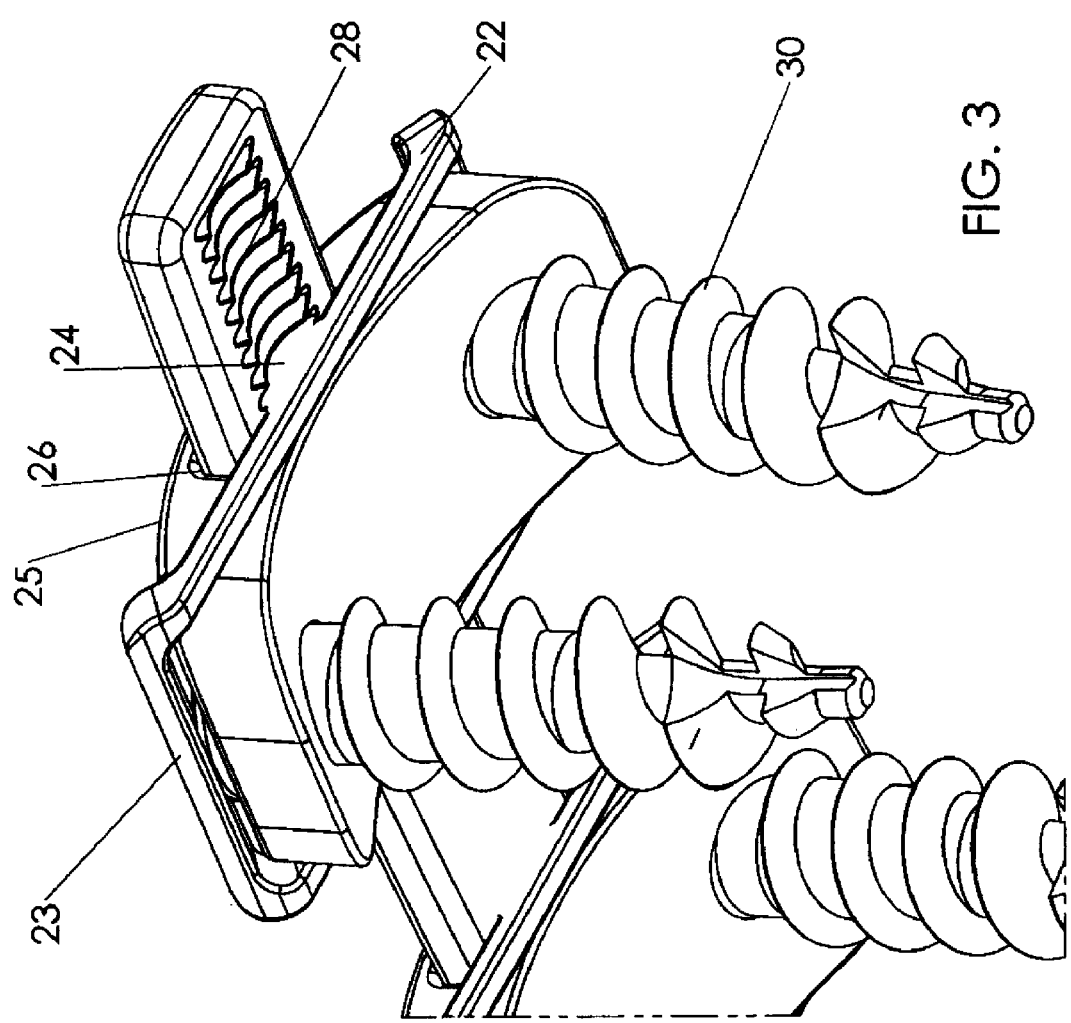
FIG. 3 is a bottom perspective of the cervical plate, screw receivers, ratchet and locking clip.

As shown in FIG. 2, the cervical plate has an intermediate bar 17 slidably attached to the free end of the shaft 11. The intermediate bar is formed in a C-shaped configuration which terminates in a left end 18 and a right end 19. The distance between right end 19 and left end 18 is sufficient to accommodate the longitudinal rail 16 acting as a guide for sliding adjustment of the intermediate bar 17 along the shaft 11. The proximal surface of the intermediate bar is dome shaped and the thickness of the ends of the intermediate bar and the height of the rail are approximately the same to provide a smooth outer surface to the implant. The intermediate bar 17 has countersunk bone screw holes 21, 21' disposed on opposite sides of the shaft 11.

Figure 4:
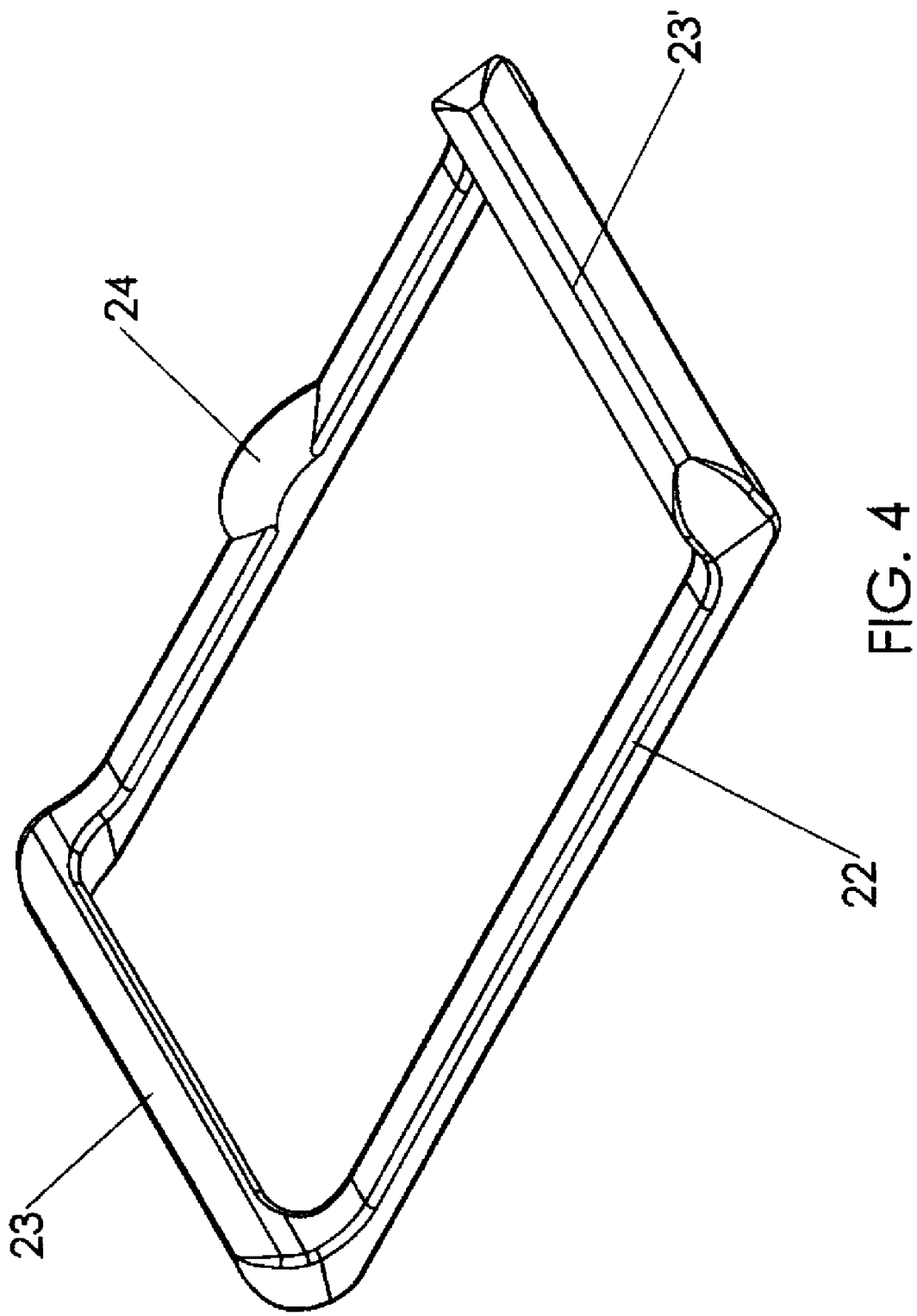
FIG. 4 is a perspective of the clip.

A continuous resilient clip 22, as shown in FIG. 4, extends over each side of the bars between the edge of the bar and the screw holes and under the shaft 11 parallel to the periphery of the bars. The a portion of the clip forms the locking mechanism that extends across the countersunk apertures as retainers 23, 23' for retaining the bone screws to prevent back-out. The clip 22 is resilient enough to allow flexing as the heads of the bone screws are seated in the apertures then rebounds on top of the screw heads. The resiliency of the clip also allows for a force fit of the clip onto the bar. The dome shaped proximal surface and the periphery of the intermediate bar provide centering and positioning tension in the clip. A pawl 24 is formed on the clip intermediate the retainers 23, 23'.

The free end 13 of the shaft is inserted through an end bar 25 which has a bore 26 shaped to slidably receive the end of the shaft. The end 27 of the longitudinal rail 16 acts as a stop when it contacts the edge of the end bar 25. The end bar 25 also has a clip 22 such as mounted on the intermediate bar. Countersunk screw holes 29, 29' accept the heads of the bone screws 30 and the retainers flex over the holes to block back out of the screws.

The distal surface 14 of the shaft has a row of grooves or scallops 28 formed across the longitudinal axis of the shaft 11. The groves or scallops are angled to form a ratchet allowing one-way movement of a bar from the free end 13 toward the lateral bar 12 at the other end of the plate. In some instances, the grooves or scallops may be cut normal to the shaft.

The tension in the clip 22 provides a close association between the distal surface of the shaft and the pawl 24. The pawl 24 engages the grooves 28 as the bars are slid along the shaft allowing a one-way movement of the bars. The portion of the clip 22 parallel to the periphery of the bars prevents movement of the bars independently of the clip.

In operation, the vertebrae are manipulated into the desired position and grafting material placed as required to compensate for removal of bone and/or disk material. The plate is fixed into place with screws first then compressed to provide some compression on the site to assist in the grafting of the spine. As the bars are slid along the shaft, the ends of the intermediate bar and the bore of the end bar maintain a close fit between the pawls on the clips and the grooves or scallops on the shaft requiring the pawls to be deflected by the grooves or scallops. Once the bars are in the desired location the ratchet prevents retrograde movement of the bars away from the head. The bone screws are driven into the spine. As the screw heads engage the apertures the retainers are flexed to permit the screw heads to seat in the apertures and released to block back-out.

It is well known that as the site heals and the adjacent vertebrae begin to graft together and as a result of the forces of gravity, there is some reduction in the span between the vertebrae. As this occurs the dynamic cervical plate can accommodate the reduction and maintain some compression because the shaft will move in the intermediate and end bars resulting in the clips moving from one ratchet tooth to the next automatically shortening the intervertebral distance. The intermediate bar has a range of travel between the lateral bar and the end bar whereas the end bar travel is limited by the end of the rail. This allows more adjustment in the intermediate vertebrae.

A second intermediate bar may be added to the free end of the plate to add stability to the compressed site and to reduce and equalize the pressure. Of course, the pawls may be omitted, and the plate may move in both directions within the bars.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

What is claimed is:

1. A dynamic spinal plate for stabilizing adjacent vertebrae comprising and elongated shaft with a proximal surface and a distal surface, a first bar and a second bar on said shaft, at least one bar movably mounted on said shaft, stop means on said elongated shaft for limiting movement of said at least one bar, said first bar and said second bar each extending transverse to said elongated shaft, screw holes adapted to seat a screw head in said first bar and said second bar on opposite sides of said elongated shaft, a clip attached to said first bar and second bar, said clip having a retainer spanning said screw holes; said distal surface of said elongated shaft has a series of transverse grooves, said clip has a pawl engaged with said grooves providing a one-way adjustment of said at least one bar along said elongated shaft.

2. A dynamic spinal plate of claim 1 wherein a second clip is attached to said second bar having a retainer spanning each of said screw holes.

3. A dynamic spinal plate of claim 2 wherein said stop means includes a longitudinal rail on said proximal surface, said second bar including C-shaped body having opposed ends, each of said ends engaging said longitudinal rail along each side of said rail for slidable movement along said shaft with said body in close contact with said elongated shaft.

4. A dynamic spinal plate of claim 2 wherein said distal surface of said shaft has a series of transverse grooves, said second clip has a pawl engaged with said grooves providing a one-way adjustment of said second bar along said elongated shaft.

5. A dynamic spinal plate of claim 2 wherein an end bar is slidably attached near said opposite end of said elongated shaft, said end bar extends transverse to said elongated shaft, screw holes in said end bar on each side of said elongated shaft, a clip fixed to said end bar having a retainer spanning each of said screw holes.

6. A dynamic spinal plate of claim 1 wherein said stop means includes a longitudinal rail on said proximal surface, at least one of said first bar and said second bar including C-shaped body having opposed ends, each of said ends engaging said longitudinal rail along each side of said rail for slidable movement along said shaft with said body in close contact with said elongated shaft.

7. A dynamic spinal plate of claim 6 wherein said distal surface of said shaft has a series of transverse grooves, said clip has a pawl engaged with said grooves providing a one-way adjustment of said at least one bar along said elongated shaft.

8. A dynamic spinal plate of claim 1 wherein said stop means includes a longitudinal rail on said proximal surface of said elongated shaft, said second bar including a body with a bore therethrough for slidable movement along said shaft with said body in close contact with said elongated shaft, said elongated shaft extending through said bore.

9. A dynamic spinal plate of claim 1 wherein said distal surface of said shaft has a series of transverse grooves, said clip has a pawl engaged with said grooves providing a one-way adjustment of said second bar along said elongated shaft.

10. A dynamic spinal plate of claim 1 wherein an end bar is slidably attached near said opposite end of said elongated shaft, said end bar extends transverse to said elongated shaft, screw holes in said end bar on each side of said elongated shaft, an end clip fixed to said end bar having a retainer spanning each of said screw holes.

11. A dynamic spinal plate of claim 1 wherein an end bar is slidably attached near said opposite end of said elongated shaft and adapted to engage said stop means, said end bar extends transverse to said elongated shaft, screw holes in said end bar on each side of said elongated shaft, an end clip fixed to said end bar having a retainer spanning each of said screw holes.

12. A dynamic spinal plate for stabilizing adjacent vertebrae comprising an elongated shaft with a proximal surface and a distal surface, said shaft having a first bar fixed at one end adapted for connection with a vertebra, said first bar extending laterally normal to said elongated shaft, screw holes in said first bar on opposite sides of said elongated shaft, said shaft having a free end, a rail extending along said proximal surface, said shaft having a set of transverse grooves formed on said distal surface, at least a second bar movably mounted near said free end, said second bar adapted for connection with an adjacent vertebra, said second bar extending laterally normal to said elongated shaft, screw holes in said second bar on opposite sides of said elongated shaft, said second bar contacting said rail, said second bar including an attached second clip, said second clip having a pawl engaging said grooves and securing said second bar along the length of said plate thereby providing one-way movement between said one bar and said second bar; and said second clip includes retainers, said retainers spanning said screw holes and partially blocking said screw holes in said second bar.

13. A dynamic spinal plate of claim 12 wherein said first bar includes an attached first clip, said first clip including retainers spanning said screw holes and partially blocking said screw holes.

14. A dynamic spinal plate of claim 12 wherein said rail terminates short of said free end of said shaft, an end bar slidably mounted on said free end, said end bar extending laterally normal to said elongated shaft, said end bar including screw holes on opposite sides of said shaft, an end clip mounted on said end bar, said end clip having a pawl engaging said grooves and securing said end bar along the length of said plate, thereby providing one-way movement between said end bar and said second bar, said rail acting as a stop for movement of said end bar.

15. A dynamic spinal plate of claim 14 wherein said end clip includes retainers, said retainers spanning said screw holes and partially blocking said screw holes.

16. A dynamic spinal plate for stabilizing adjacent vertebrae comprising an elongated shaft with a proximal surface and a distal surface, said shaft having a first bar fixed at one end adapted for connection with a vertebra, said first bar extending laterally normal to said elongated shaft, screw holes in said first bar on opposite sides of said elongated shaft, said first bar includes an attached first clip, said first clip including retainers spanning said screw holes and partially blocking said screw holes, said shaft having a free end, a rail extending along said proximal surface, said shaft having a set of transverse grooves formed on said distal surface, a second bar movably mounted near said free end, said second bar adapted for connection with an adjacent vertebra, said second bar extending laterally normal to said elongated shaft, screw holes in said second bar on opposite sides of said elongated shaft, said second bar contacting said rail, said second bar including an attached second clip, said second clip having a pawl engaging said grooves and securing said second bar along the length of said plate, said second clip including retainers, said retainers spanning said screw holes and partially blocking said screw holes in said second bar, thereby providing one-way movement between said one bar and said second bar, an end bar slidably mounted on said free end, said end bar extending laterally normal to said elongated shaft, said end bar including screw holes on opposite sides of said shaft, an end clip mounted on said end bar, said end clip having a pawl engaging said grooves and securing said end bar along the length of said plate, said end clip including retainers, said retainers spanning said screw holes and partially blocking said screw holes in said end bar.

17. A dynamic spinal plate of claim 16 wherein said rail terminates short of said free end of said shaft, said rail acting as a stop for movement of said end bar.

\* \* \* \* \*